United States Patent
Estebe

(10) Patent No.: US 10,031,094 B2
(45) Date of Patent: Jul. 24, 2018

(54) METHOD FOR PREDICTING TEMPERATURES WHICH ARE TOLERABLE BY A COMPONENT, A PIECE OF EQUIPMENT OR AN AIRPLANE STRUCTURE

(71) Applicant: Airbus Operations SAS, Toulouse (FR)

(72) Inventor: Bruno Estebe, Gragnague (FR)

(73) Assignee: AIRBUS OPERATIONS SAS, Toulouse (FR)

( * ) Notice: Subject to any disclaimer, the term of this patent is extended or adjusted under 35 U.S.C. 154(b) by 0 days.

(21) Appl. No.: 15/285,666

(22) Filed: Oct. 5, 2016

(65) Prior Publication Data

US 2017/0101195 A1    Apr. 13, 2017

(30) Foreign Application Priority Data

Oct. 12, 2015 (FR) ...................................... 15 59691

(51) Int. Cl.

| | |
|---|---|
| B64F 5/00 | (2017.01) |
| G07C 5/08 | (2006.01) |
| G06F 17/50 | (2006.01) |
| G06F 17/18 | (2006.01) |
| G01N 25/00 | (2006.01) |
| B64F 5/60 | (2017.01) |

(52) U.S. Cl.
CPC .............. *G01N 25/00* (2013.01); *B64F 5/60* (2017.01); *G06F 17/18* (2013.01); *G06F 17/5009* (2013.01); *G07C 5/0841* (2013.01); *G06F 17/5095* (2013.01)

(58) Field of Classification Search
CPC ..... G01N 25/00; G06F 17/5009; G06F 17/18; G06F 17/5095; G07C 5/0841; B64F 5/60
See application file for complete search history.

(56) References Cited

U.S. PATENT DOCUMENTS

| | | | |
|---|---|---|---|
| 2012/0179326 A1* | 7/2012 | Ghelam | G05B 17/02 701/31.9 |
| 2012/0303572 A1* | 11/2012 | Isozaki | G06K 9/6277 706/52 |

OTHER PUBLICATIONS

French Search Report, dated Aug. 10, 2015, priority document.

(Continued)

*Primary Examiner* — Anne M Antonucci
(74) *Attorney, Agent, or Firm* — Greer, Burns & Crain, Ltd.

(57) ABSTRACT

A method for predicting temperatures tolerable by a component, a piece of equipment or a vehicle structure. This method includes the steps of determining, for each piece of equipment, component or structure of the vehicle, such as an airplane, a temperature spectrum depending on a plurality of extrinsic parameters measured during a full operating cycle of the airplane, by taking into account, for each piece of equipment, component or structure, possible combinations of the extrinsic parameters and setting aside unlikely combinations of the extrinsic parameters, determining, for each piece of equipment, component or structure, the probability of occurrence of the spectrum during the full airplane operating cycle, and defining a database including the temperature spectra so as to predict the lifetimes of the piece of equipment, component or structure and redefine weather and operational standards indicating extreme temperatures and their probability of occurrence obtained with the measured extrinsic parameters.

6 Claims, 2 Drawing Sheets

(56) References Cited

OTHER PUBLICATIONS

"Reliability Estimation in Random Environment: Different Approaches", Sorin Et al., Jan. 1, 2007.
"Calculatin Transient Thermal Load of ECUs in Engine Compartment by Applying Simplified Physical Models", Decker et al., Mar. 6, 2012.
"OLMOS in GAF MRCA Tornado—10 years of experience with on-board life usage monitoring" Broede and H. Pfoertner J., Jul. 6, 1997.
"RTO Techinical Report 44 Performance Prediction and Simulation of Gas Turbine Engine Operation" O'brien, May 19, 2015, pp. 1-357.
"Fuzzy logic aircraft environment controller", Dobrescu et al., Jun. 27, 2004.

\* cited by examiner

METHOD FOR PREDICTING TEMPERATURES WHICH ARE TOLERABLE BY A COMPONENT, A PIECE OF EQUIPMENT OR AN AIRPLANE STRUCTURE

CROSS-REFERENCES TO RELATED APPLICATIONS

This application claims the benefit of the French patent application No. 1559691 filed on Oct. 12, 2015, the entire disclosures of which are incorporated herein by way of reference.

TECHNICAL FIELD

The invention lies in the thermal analysis with a view to predicting the range of temperatures tolerated by a component, a piece of equipment or a structure of a vehicle such as an airplane, a helicopter, a rocket, a satellite, a train, a motor vehicle, a bus or a boat.

The invention relates also to a device and a computer program stored on a storage medium intended to implement the method according to the invention.

These temperature ranges are then used, for example, to compute the loads and structural stress fields for environmental qualification, in particular the hot/cold temperature range of the materials and pieces of equipment, or even to check the operation durability of these pieces of equipment and of these structures.

BACKGROUND OF THE INVENTION

Thermal analysis relates to all the means making it possible to estimate the temperatures tolerated by a component, a piece of equipment or a structure of a vehicle. This estimation relies on an analysis of the laws of the physics thermal exchanges (phenomena of conduction, diffusion, convection, radiation, advection), and the representation thereof in mathematical form, making it possible to solve the heat equation. One of the means known for performing this estimation comprises solving mathematical models by digital means, relying on the finite differences, finite elements or finite volume methods.

The thermal models of the prior art intended to predict the temperature ranges for a component, a piece of equipment or a structure of a vehicle such as an airplane, for example, rely on a number of intrinsic properties of the vehicle such as its geometry, its materials, and the performance levels of its systems, and on extrinsic parameters such as climatic flows, number of passengers, operations specific to the airlines when the vehicles are airplanes, the external paint work, (the livery) of the airplane, the operational flight profile, the maintenance operations, the nature of the fuel, the quantities of flights, etc. These thermal models are either nodal models relying on the finite differences method, or models relying on the finite elements or even finite volumes technique. These thermal models rely also on standardized extrinsic parameters which depend on the climatic conditions, the standard airplane operations, or even standardized flight profiles. The extrinsic parameters which are introduced into the model are defined so as to cover the possible range of climatic environments, the possible range of operations on the vehicle, possible liveries, from very light to very dark, typical flight profiles (for example, short haul, medium haul, long-haul mission, etc.), and the number of passengers in as much as a number of scenarios can be considered according to the load factor. Thus, for example, the climatic environment range must cover all the conditions which could be encountered at all the world airports frequented by the vehicle, and all the seasons, from extreme cold to extreme heat, and do so for all the altitudes at which the airplane could fly.

For the extreme hot and cold cases, standards have been defined on the basis of documents describing the extreme climatic conditions such as, for example, military standards documents, or even environmental climatic standards. These standards describe the climatology of the extreme day considered (air temperature, winds, solar radiations). For the liveries of the airlines, theoretical levels are considered which take into consideration the fact that dark colors absorb heat more than light colors. Ultimately, the temperatures thus estimated on the components, pieces of equipment or structures of a vehicle are assumed to be limited cases, and their probability of being exceeded is extremely rare because it depends on a stacking up of critical considerations, of paintwork, climate and operations.

Regarding the analyses of the life time of the components, pieces of equipment or structures of a vehicle, the prior art techniques rely also on a mixture of standardized cases including a certain percentage of tropical or polar flights, or flights in a standard atmosphere, with a paintwork of a given color. Here again the probability of actually obtaining this combination is not determined, the margins are not therefore known.

Another drawback with these techniques stems from the fact that the real conditions of use of the vehicles are such that the theoretically computed levels are far from being reached. Also, the methods for the prior art do not make it possible to know the probability of reaching these temperatures, and therefore of defining the margins in relation to the reality of the operations.

The invention aims to mitigate the drawbacks of the prior art described above by means of an analysis method based on real measurements of the flight conditions of an airplane on real climatic data measuring during the flights.

SUMMARY OF THE INVENTION

The invention recommends a method for measuring and analyzing a plurality of extrinsic parameters relating to the climatic conditions encountered by the vehicle with a view to predicting the range of temperatures supported by a component, a piece of equipment or a structure of the vehicle. This method comprises determining, for the piece of equipment, component or structure of the vehicle, a temperature probability spectrum as a function of the plurality of extrinsic parameters measured and/or estimated during a determined period of operation of the vehicle so as to predict the temperature influence on the piece of equipment, component or structure in terms of lifetime and/or structural stress.

By virtue of the invention, the prediction of the range of temperatures that can be tolerated by a component, a piece of equipment or a structure of a vehicle relies on an extended definition of the extrinsic parameters, thus making it possible to introduce the notion of statistical distribution of their values, rather than considering standardized extreme or typical cases. Consequently, the result of the analysis is no longer just a temperature level reached for each case, but a temperature spectrum, according to the probability of occurrence thereof, for each piece of equipment, component, structure, and over the full range of operation of the vehicle, by taking into account the possible combinations and by setting aside the unlikely combinations.

When the vehicle is a flying vehicle, an airplane or a helicopter, for example, the plurality of extrinsic parameters further comprises a climatic data of the airports frequented in flight, and the operations specific to each airport such as the rotation time between two flights, the taxiing time between the set-off point and the take-off runway.

According to another feature of the invention, for each particular phase of the flight of the airplane, the temperature spectrum is determined as a function of a specific combination of extrinsic parameters.

Preferably, each specific combination comprises a reduced number of extrinsic parameters so as to improve the accuracy and the definition of the temperature range predictions.

The method according to the invention is implemented by means of a device for measuring and analyzing a plurality of extrinsic parameters relating to the climatic conditions encountered by a vehicle with a view to predicting the range of temperatures to which a piece of equipment or a structure of the vehicle will be subjected, comprising a computation module and an analysis module suitable for determining, for the piece of equipment, component or structure of the vehicle, a temperature probability spectrum as a function of the plurality of extrinsic parameters measured and/or estimated during a determined period of operation of the vehicle so as to predict the influence of the temperature on the piece of equipment, component or structure in terms of life time and/or structural stress.

BRIEF DESCRIPTION OF THE DRAWINGS

Other features and advantages of the invention will emerge from the following description, taken as a nonlimiting example, with reference to the attached figures in which.

DETAILED DESCRIPTION OF THE PREFERRED EMBODIMENTS

The invention will be described in a particular example of implementation of the method according to the invention intended to define a thermal and operational model which would introduce extremely hot or extremely cold temperatures, with a known probability of occurrence. This model is established through the measurement and the analysis of a large number of climatic conditions which could be encountered by an airplane for a large number of successive flights made by this airplane during a full period of operation of the airplane, a year, for example, by taking into consideration the climatic conditions of the airports frequented and the operations specific to the airport such as, for example, the rotation time between two flights, the taxiing time between the set-off point and the take-off runway, or any other parameter that might influence the temperatures.

A thermal model should be understood to be a numerical model (for example, of finite differences type), making it possible to represent all the heat exchanges affecting a component, a piece of equipment or a structure of a vehicle in the form of the heat equation and the solving of which makes it possible to estimate the temperatures thereof. The thermal models developed within the context of the invention are of transient nature in as much as they allow for the temporal estimation of temperature changes, resulting from fluctuation of heat flux, of diffusion of the heat through the materials, of heat accumulated by the thermal inertia thereof.

Figure 1:
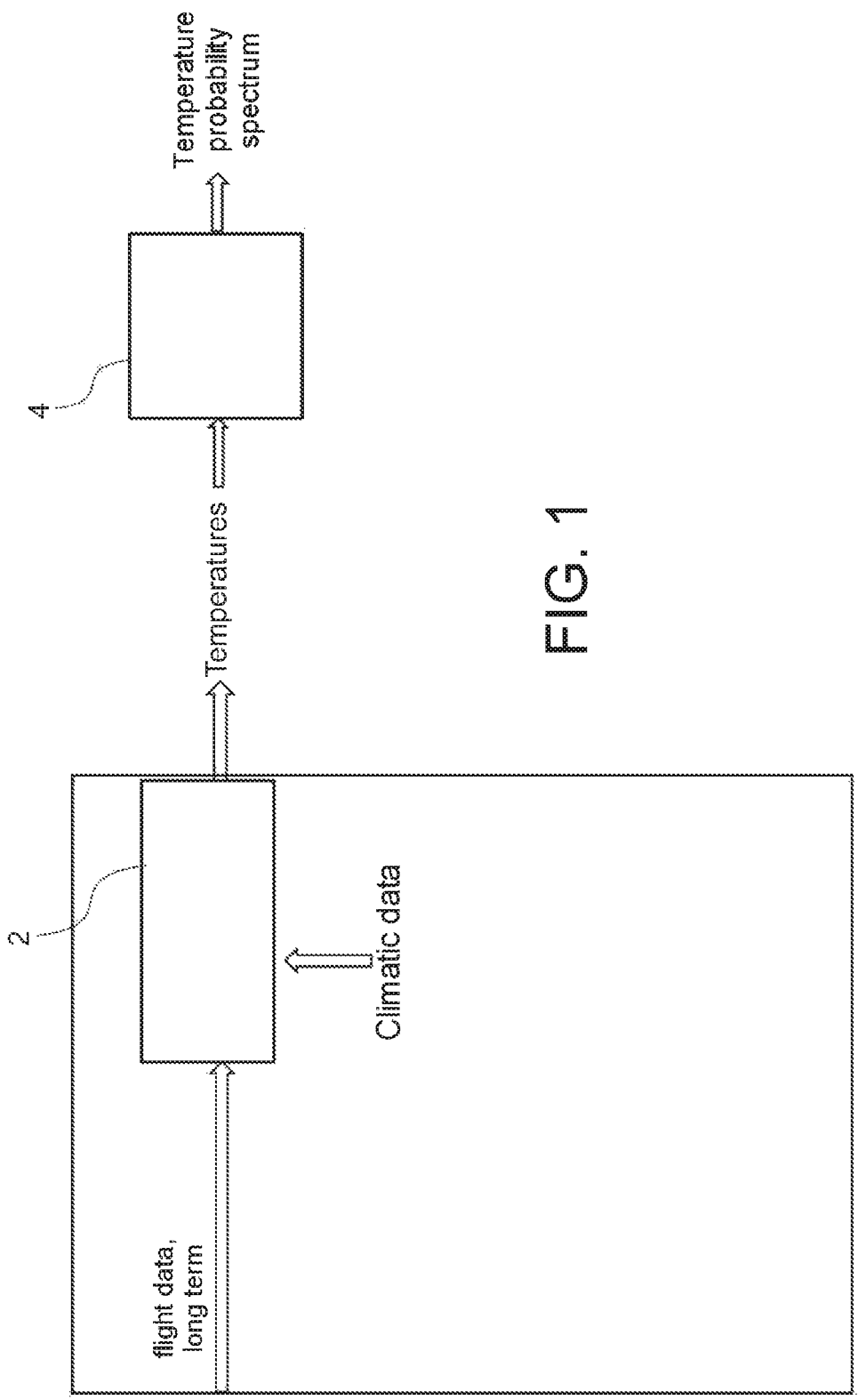
FIG. 1 illustrates a block diagram of a device intended to implement the method according to the invention.

The device of FIG. 1 comprises a computation module 2 intended to generate a thermal model and an analysis module 4 intended to compute a temperature probability spectrum.

As is schematically illustrated by FIG. 1 for the computation of the thermal model, the inputs of the computation module 2 comprise long term flight data, climatic data measured and/or estimated during these flights such as, for example, the air temperature T, the ground temperature T, the wind temperature T of the different airports, data relating to the geographic position of the airplane (longitude, latitude, altitude), the date, time, incidence, heading and speed of the airplane. The processing of these input data by the computation module 2 provides extremely hot or extremely cold temperatures. These temperatures are then analyzed by the analysis module 4 to provide a temperature spectrum.

Figure 2:
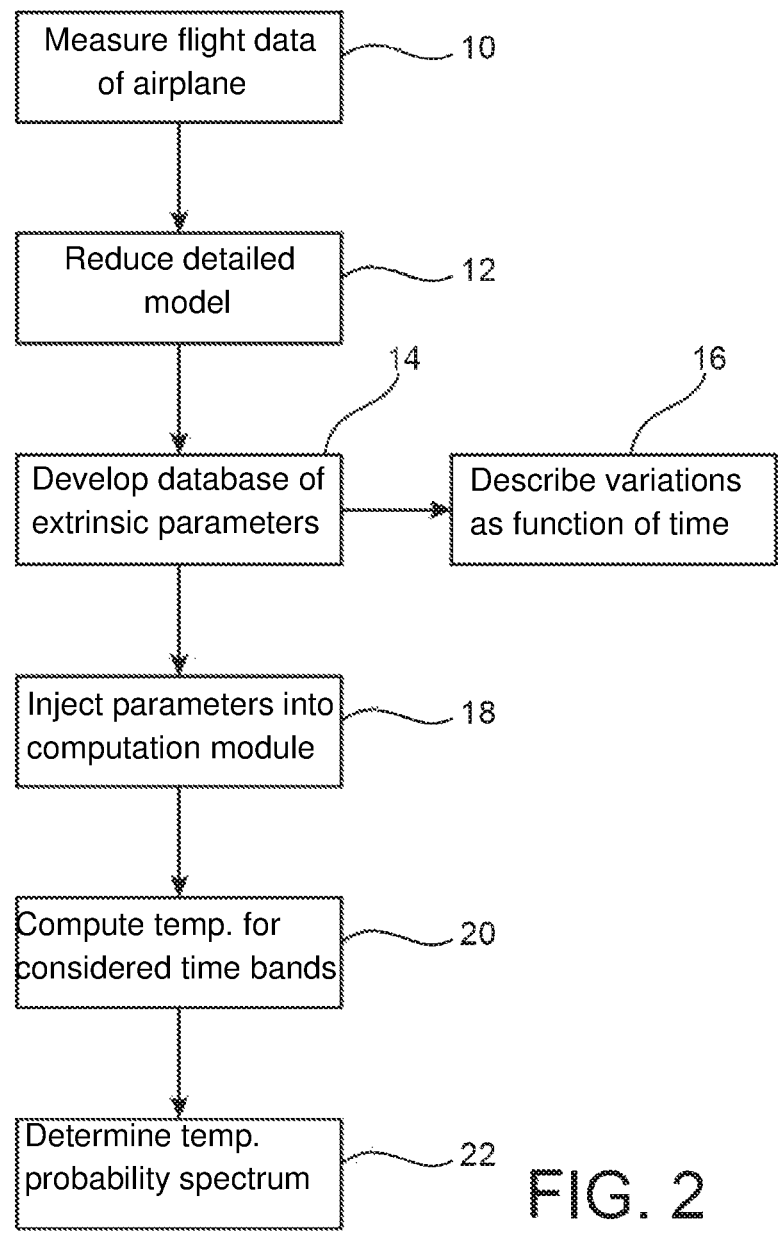
FIG. 2 schematically illustrates the steps of a particular mode of implementation of the method according to the invention.

FIG. 2 schematically illustrates the steps of the computation of the thermal model. In step 10, the flight data of the airplane are measured over a particular flight or operation phase. This step 10 comprises producing a transient thermal model (for example, numerical, based on the finite volume method). This thermal model represents the heat exchangers in the structures, the pieces of equipment and compartments which constitute the area of study (conduction and diffusion, thermal inertia in the structural materials, convection with the ambient air of the compartments, infra-red radiation between the walls of the compartments, and vector flows provided by ventilations or air movements). This includes the heat dissipations of the internal components (electrical, electronic, motors, hydraulic or thermal systems or similar whose hot walls discharge their heat into area of study). Finally, the thermal model includes the heat exchangers with the outside environment (solar, terrestrial and atmospheric radiation fluxes, convection with atmospheric air, kinetic heating in flight) and does so in order to represent the sequence of a full flight in a transient manner.

The detailed thermal model is defined so as to finally represent the heat exchangers and not just the predominant phenomenon with a fairly fine spatial resolution to estimate the thermal gradients. Thus, for example, in the example of use of a finite volumes model the size of the representative volumes required can reach a few millimeters to a few centimeters, in the scale representing a full airplane compartment of several meters.

The detailed thermal model comprises properties and conditions at the limits which are intrinsic to the design of the airplane (for example, the design of the parts, their geometrical characteristics, thicknesses, materials, etc.). It also comprises extrinsic limiting conditions, not linked to the design of the airplane but to its operational use, for example, limiting conditions modelling the climatic flows, or else influenced by the definition of the in-flight trajectory, the number of passengers onboard, the volumes of fuel onboard, the external paintwork specific to the airline, etc.

In step 12, the detailed model is reduced by retaining the extrinsic limiting conditions as input parameters common to the detailed and reduced models.

This step comprises developing a simplified transient thermal model, from the detailed model developed in step 10. Concerning the subsequent steps, the prerequisite of this model reduction relies on the fact that the detailed and reduced models must share the same extrinsic limiting conditions. For example, in the case of a finite volume model, it is possible to reduce the model by grouping together the volumes to which are subjected to the same limiting conditions (intrinsic or extrinsic) as the adjacent volumes. The aim of this step is to produce a sufficiently rapid thermal model to be resolved so as to extend the time band of resolution of a flight (for example, 1 to 12 hours of operation time) to a full year of operations (for example, 5000 hours), even several years.

To check the quality of reduction of the thermal model produced, an acceptance test is performed to check the resolution time time-saving on a computation test case (for example for the duration of a flight), and to quantify the temperature approximations induced by the resolution loss of the simplified model compared to the detailed model deriving from step 10, and this is done in order to best produce the time-saving/resolution trade-off, according to the accuracy required by the study.

Step 14 comprises developing a data base of the extrinsic parameters to cover a full period of operation of the airplane. This period can be, for example, a year or more.

Step 16 comprises describing the variations of the extrinsic parameters as a function of time during the full period of operation of the airplane. This description takes into account:
the altitude, the latitude and the longitude of the trajectory of the airplane,
the speed of the airplane, the heading relative to the North,
the climatic flux: air temperature of the solar and albedo flux (vectors) downward and upward infra-red radiations, speed, direction and turbulence of the winds,
the incidence of the airplane.

The description of step 16 also takes into account operations of the airplane on the ground so as to define the limiting conditions of use of its various pieces of equipment, and of the airport infrastructures. These operations are, for example:
the filling of the fuel tanks (time of filling, duration, quantities per tank, temperature),
time, duration of use of the power auxiliaries, of the ground means of the airport (air, electricity),
time, duration of disembarkation/embarkation of the passengers, number of passengers and crew members,
the rotation time between two flights, the taxiing time between the set-off point and the take-off runway, or any other parameter that might influence the temperatures.

For each vehicle considered, the description of step 16 also takes into account extrinsic variables linked to the customization of the airplane by the airline such as, for example, the optional onboard pieces of equipment, the livery (external paintwork) of the airplane and the thermal-optical properties thereof.

Step 18 comprises injecting into the computation module two extrinsic parameters defined in the sequential computation of the reduced model from step 12.

To this end, the data base from step 14 will be used to generate the extrinsic limiting conditions over all of the range of resolution time (from several flights to one or more years for the airplane model (or models)) studied. For example, for a finite volumes model of the airplane compartment, these extrinsic limiting conditions will be defined as temporal tables of solar flux, air temperature and atmospheric radiation values, which are input data for the reduced thermal model.

Step 20 comprises computing the temperature for all of the time band considered.

In order to generate the temperature results and optimize the resolution thereof, particular attention will be paid to controlling the computation time steps. In effect, the fineness thereof conditions the accuracy of the analyses possible in the subsequent steps, in particular the high frequencies (small time steps) make it possible to finely estimate the probability of rare events (to the detriment of the effect of model resolution time), and the relaxation of the resolution step at low frequencies (high time steps) during the long flight phase or on the ground, may make it possible to improve the effect of resolution time. The use of a constant (or even variable) time step and the range of values defined for this time step therefore results from a trade-off between the performance of the reduced model assessed in step 12, the accuracy required for the subsequent steps, and the good numerical convergence reduced thermal model in the example of a model of finite volumes type.

Step 22 comprises determining, from the computation results of step 20, a temperature probability spectrum for each element for which the thermal model of step 12 is representative (structure, piece of equipment, compartment, etc.).

For example, by analyzing the large number of temperatures generated by all of the time band considered, it is possible to describe this result, not in the form of a chronological histogram, but in the form of one or more statistical distributions indicating, for example:
the probability of being below or above a given temperature—within the [minimum-maximum] range of the possible temperatures computed
the probability of being at a given temperature,
the probability of reaching the maximum or minimum temperature and the extreme value,
the temperature value with a given probability.

To this end, it is also possible to link the results with the data bases obtained in step 16, so as to improve the possible statistical processing operations.

For example, it is possible to estimate the probability or the statistical distribution of the temperatures in a specific phase of operations or in specific flights (for example, the statistical distribution of the temperatures at the time of landing or at the time of starting up of the electrical systems).

Note that the data collected are stored in the data base and can be used to:
redefine new climatic and operational standards which would introduce extremely hot or extremely cold temperatures, with a known probability occurrence, and of which the set of extrinsic parameters making it possible to obtain them can be determined,
feeding the lifetime analyses, with a thermal spectrum based on the real or theoretical probability, and no longer over a limited number of discrete cases, for a type of airplane, for an airline or a fleet of vehicles operated in certain regions, etc.

The method according to the invention makes it possible to focus on a flight phase or a particular operation. It is then possible to define the temperature spectrum which could be encountered by the vehicles of a given airline, for example in approach phase, at 10 000 meters of altitude with a confidence interval of 80%. By improving the statistical knowledge of the temperature distributions, it is possible to anticipate reducing the number of cases requiring particular investigations, by controlling the margins, instead of the prior art approach which inclusively analyzes the outer limit cases for which the probability is unproven or unknown.

By virtue of this statistical analysis relying on temperature spectra, it is possible to define a small number of combinations of extrinsic parameters to be analyzed for the development of an airplane (loads, analyses of structural stresses or of system or equipment performance levels). This short list of combined parameters can then be introduced into the native (non-reduced) thermal model, so as to improve the accuracy and the definition of the temperature range predictions.

The method according to the invention thus makes it possible to determine the margins between the temperatures observed (or simulated) in service and the design basis temperatures. This method can also be used to investigate design basis of sensitive components, with small temperature margin.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for predicting the range of temperatures tolerated by a component, a piece of equipment or a structure of a vehicle comprising the following steps:
    measuring, by a computer processor, a plurality of extrinsic parameters relating to the climatic conditions and encountered by the vehicle,
    storing the plurality of extrinsic parameters over a determined period of operation of the vehicle in a database,
    determining, by a computer processor, for said piece of equipment, component or structure, a temperature probability spectrum as a function of the plurality of extrinsic parameters measured during the determined period of operation of the vehicle, in which the prediction of the range of temperatures is made over the full range of operation of the vehicle is a function of a specific combination of extrinsic parameters, according to the probability of occurrence thereof, for each piece of equipment, component, structure, by taking into account the possible combinations and by setting aside the unlikely combinations, and
    linking the results of said determining with the database, wherein said determining takes place over controlled constant or variable computation time steps to control a resolution of said determining.

2. The method as claimed in claim 1, in which said plurality of extrinsic parameters comprises the climatic conditions encountered by the vehicle during the determined period.

3. The method as claimed in claim 2, in which, when said vehicle is an airplane, said plurality of extrinsic parameters further comprises the climatic data of the airports frequented in flights of the airplane, and the operations specific to each airport such as the rotation time between two flights, taxiing time between the set-off point and the take-off runway.

4. The method as claimed in claim 3, in which said specific combination of extrinsic parameters comprises a reduced number of parameters so as to improve the accuracy and the definition of the temperature range predictions.

5. A device for predicting the range of temperatures to which a piece of equipment or a structure of a vehicle will be subjected, the device comprising:
    a computation module including a computer processor having inputs for receiving measured values for extrinsic parameters relating to the climatic conditions encountered by the vehicle, during a determined period of operation of the vehicle, said computation module being configured to produce a prediction of the range of temperatures over the full range of operation of the vehicle as determined as a function of a specific combination of extrinsic parameters, according to its probability of occurrence, for each piece of equipment, component, structure, by taking into account the possible combinations and by setting aside the unlikely combinations, and to compute a thermal model and to transmit the thermal model to an analysis module including the computer processor,
    a database for storing the measured values for extrinsic parameters over the determined period of operation, the analysis module being configured to determine, for said piece of equipment, component or structure, a temperature probability spectrum as a function of the thermal model provided by the computation module,
    the analysis module being further configured to link the results of the determining a probability spectrum with the database,
    wherein the determining a probability spectrum takes place over controlled constant or variable computation time steps to control a resolution of the determining.

6. A non-transitory computer readable medium storing instructions executable by a computer processor for performing the steps of a method for predicting the range of temperatures tolerated by a component, a piece of equipment or a structure of a vehicle comprising the following steps:
    measuring a plurality of extrinsic parameters relating to the climatic conditions and encountered by the vehicle,
    storing the plurality of extrinsic parameters over a determined period of operation of the vehicle in a database,
    determining, for said piece of equipment, component or structure, a temperature probability spectrum as a function of the plurality of extrinsic parameters measured during the determined period of operation of the vehicle, in which the prediction of the range of temperatures is made over the full range of operation of the vehicle is a function of a specific combination of extrinsic parameters, according to the probability of occurrence thereof, for each piece of equipment, component, structure, by taking into account the possible combinations and by setting aside the unlikely combinations, and
    linking the results of said determining with the database, wherein said determining takes place over controlled constant or variable computation time steps to control a resolution of said determining.

* * * * *